(12) United States Patent
Clifton et al.

(10) Patent No.: US 7,387,032 B2
(45) Date of Patent: Jun. 17, 2008

(54) METHODS AND APPARATUS FOR MEASURING THE VISCOELASTIC RESPONSE OF VOCAL FOLD TISSUES AND SCAFFOLDS ACROSS A FREQUENCY RANGE

(75) Inventors: Rodney J. Clifton, Barrington, RI (US); Tong Jiao, Pawtucket, RI (US); Christopher Bull, Rehoboth, MA (US)

(73) Assignee: Brown University, Providence, RI (US)

( * ) Notice: Subject to any disclaimer, the term of this patent is extended or adjusted under 35 U.S.C. 154(b) by 666 days.

(21) Appl. No.: 11/082,305

(22) Filed: Mar. 16, 2005

(65) Prior Publication Data
US 2006/0207343 A1 Sep. 21, 2006

(51) Int. Cl.
*G01N 3/24* (2006.01)
*G01L 1/24* (2006.01)

(52) U.S. Cl. .......................... 73/841; 73/800
(58) Field of Classification Search ............... 73/54.37, 73/54.39, 800, 841
See application file for complete search history.

(56) References Cited

U.S. PATENT DOCUMENTS

| | | | | |
|---|---|---|---|---|
| 4,539,838 | A * | 9/1985 | Fraleigh | 73/54.23 |
| 5,357,783 | A * | 10/1994 | Eschbach | 73/54.33 |
| 2002/0194900 | A1* | 12/2002 | Hajduk et al. | 73/61.49 |
| 2003/0183016 | A1* | 10/2003 | Prescott et al. | 73/841 |

OTHER PUBLICATIONS

Jia, X, et al., "Synthesis and Characterization of in Situ Cross-Linkable Hyaluronic Acid-Based Hydrogels with Potential Application for Vocal Fold Regeneration", Macromolecules, vol. 37, 2004, pp. 3239-3248.*

Titze, I.R. et al., "Methodology for Rheological Testing of Engineered Biomaterials at Low Audio Frequencies", The Journal of the Acoustical Society of America, vol. 115, Issue 1, Jan. 2004, pp. 392-401.*

(Continued)

*Primary Examiner*—Daniel S Larkin
(74) *Attorney, Agent, or Firm*—Harrington & Smith, PC (57) ABSTRACT

In one aspect the present invention concerns methods and apparatus for measuring the mechanical properties of soft materials across a frequency regime. In particular, the present invention concerns methods and apparatus using torsional waves to measure the mechanical properties of vocal fold tissue and candidate materials for use in human vocal fold reconstruction. In embodiments of the present invention, sample material is placed between two plates whose sides are faceted. One of the plates is attached to the shaft of a galvanometer, and the plate is twisted back and forth through angles of up to ±6° at frequencies of up to 2500 Hz. If required, the assembly may be enclosed in an environmental chamber to maintain the temperature and relative humidity of the sample at the conditions experienced by vocal folds in a living human or animal. The rotations of the top and bottom plates are monitored by an optical lever technique in which laser beams, reflected off the faceted faces of the plates, are captured by photodiode detectors. The experimentally determined amplification factor is obtained as the ratio of the amplitude of the rotation of the top plate divided by the corresponding amplitude of the bottom plate. The shear modulus and loss angle, which describe the mechanical properties of the sample, are then obtained from the experimental data gathered by the apparatus.

31 Claims, 3 Drawing Sheets

OTHER PUBLICATIONS

Hemler, R.J.B., et al., "A New Method for Measuring Mechanical Properties of Laryngeal Mucosa", Eur Arch☐☐Otorhinolaryngol, vol. 258, 2001, pp. 130-136.*

Chan, R.W., et al., "Viscoelastic Shear Properties of Human Vocal Fold Mucosa: Theoretical Characterization Based on☐☐Constitutive Modeling", The Journal of the Acoustical Society of American, vol. 107, Issue 1, Jan. 2000, pp. 565-580.*

Chan, R.W., et al., "Viscoelastic Shear Properties of Human Vocal Fold Mucosa: Measurement and Emperical Results", The Journal of the Acoustical Society of America, vol. 106, Issue 4, Part 1, Oct. 1999, pp. 2008-2021.*

Brodt, M., et al., "Apparatus for Measuring Viscoelastic Properties Over Ten Decades: Refinements", Rev. Sci. Instrum., vol. 65, Issue 11, Nov. 1995, pp. 5292-5297.*

* cited by examiner

METHODS AND APPARATUS FOR MEASURING THE VISCOELASTIC RESPONSE OF VOCAL FOLD TISSUES AND SCAFFOLDS ACROSS A FREQUENCY RANGE

TECHNICAL FIELD

The present invention generally concerns methods and apparatus for measuring mechanical properties of soft materials across a frequency range and more particularly concerns methods and apparatus for measuring the mechanical properties at human phonation frequencies of both human vocal fold tissue and candidate materials for use in human vocal fold reconstruction.

BACKGROUND

During normal speech, human vocal folds sustain more than 100 high impact collisions each second. Voice overuse may generate nodules on the outer layer of the vocal folds—the so-called superficial lamina propria ("SLP"). In other cases, pathological conditions may render part of the tissue cancerous. In any case, whether the tissue is damaged by overuse or by surgical removal of cancerous tissue, the resulting scar tissue lacks the pliability of the original tissue and voice quality is often seriously reduced.

Over the past few years, significant research effort has been directed toward using tissue engineering approaches to regenerate vocal fold vibratory tissue that responds as normal SLP. As a first step toward developing suitable replacement materials it is important to understand the mechanical response of the natural tissue that the materials will replace, as well as the mechanical response of replacement materials at frequencies of human phonation—approximately 100-900 Hz.

In one known method, the viscoelastic properties of human vocal folds were measured by subjecting the full thickness of the vocal folds (i.e. the lamina propria (LP)) to torsional oscillations in a parallel-plate rheometer. See, for example, R. W. Chan and I. R. Titze, "Viscoelastic Shear Properties of Human Vocal Fold Mucosa: Measurement Methodology and Empirical Results," J. Acoust. Soc. Am., No. 106, 1999, pp. 2008-2001; and R. W. Chan and I. R. Titze, "Viscoelastic Shear Properties of Human Vocal Fold Mucosa: Theoretical Characterization Based on Constitutive Modeling," J. Acoust. Soc. Am., No. 106, 2000, pp. 565-580. From these experiments the frequency-dependent storage (shear) modulus and viscosity of the LP over frequencies ranging from 0.01 to 10 Hz was obtained. Notably, this frequency range lies well below the frequency range of human phonation. Measurements at 15 Hz did not follow the trend lines of the results at lower frequencies and were deemed, by the authors, to be "marginally acceptable".

An important conclusion from the Chan and Titze (1999, 2000) experiments is that the shear modulus of human vocal folds is very low. For most subjects the shear modulus $G_1$ at a frequency of 10 Hz ranges from approximately 10 to 100 Pa. The elastic shear wave speed $c_s = \sqrt{G_1/\rho}$ for a material with a shear modulus $G_1 = 100$ Pa and a density $\rho = 1000$ kg/m³ is approximately 30 cm/s. Because this wave speed is so small relative to wave speeds in most solid materials, one can expect that strong limitations will be imposed on the maximum frequency for which the mechanical properties of the sample can be inferred by means of the usual interpretation of rheometric tests—based on assuming that the stress is nominally uniform through the thickness of the sample. For solid samples the latter assumption holds when the time required for roundtrip transit of stress waves through the thickness of the sample is much less than the period of a single oscillation, i.e. for $$f \ll \frac{c_s}{2h} \quad (1)$$

where h is the sample thickness and f is the driving frequency. For human LP with a thickness h=0.03 cm, as used by Chan and Titze (1999, 2000), the limitation (1) becomes f<<500 Hz or, say, f<30 Hz. Even lower limits on allowable frequencies are obtained for samples with shear moduli near the lower limits of the range of measured values. Moreover, the SLP is known to be more compliant than the intermediate and deep layers of the LP so the measured shear moduli for the full thickness of the LP are expected to be higher than those for the SLP.

Analogously, for fluid samples, a requirement that stresses due to sample inertia are small relative to those due to sample viscosity leads to the limitation (See, for example, H. Schlichting, Boundary Layer Theory, 4th Ed., McGraw-Hill, New York, 1960)

$$f \ll \frac{2\eta}{2\pi\rho h^2} \quad (2)$$

where $\eta$ is the viscosity of the sample. From viscosity measurements of Chan and Titze (1999, 2000) the frequency dependent viscosity of human LP can be described approximately by $\eta = \eta_0 f^{-0.85}$ with $\eta_{0=1.0}$ Pa·s. Substitution of this expression for $\eta$ into (1.2) gives the limitation f<<83 Hz or, say, f<10 Hz.

Whether the frequency limitation is obtained from a constraint of type (1) or (2) it appears that the frequencies for which the viscoelastic properties of human SLP can be measured by standard rheometric methods are likely to be below the frequencies of human phonation. Other methods for measuring viscoelastic properties at high frequencies include electromagnetic torsion methods (see Brodt, et al., "Apparatus for Measuring Viscoelastic Properties Over Ten Decades: Refinements, Review of Scientific Instruments, No. 66, 1995, pp. 5292-5297); electromechanical tensile test methods (R. J. Hemler et al., "A New Method for Measuring Mechanical Properties of Laryngeal Mucosa," Eur. Arch. Otorhinolaryngol No. 258, 2001, pp. 130-136); and stress-controlled rheometer methods at low audio frequencies (I. R. Titze, et al., "Methodology for Rheological Testing of Engineered Biomaterials at Low Audio Frequencies," J. Acoust. Soc. Am., No. 115, 2004, pp. 392-401). While all of these methods have attractive features they all neglect wave propagation in the sample. Consequently, they all have frequency limitations similar to those of equations (1) and (2), although the upper limit on allowable frequencies may be extended by using smaller samples.

An alternative approach, based on the analysis of longitudinal waves in viscoelastic cylindrical rods, has been introduced (see Jia, et al., "Synthesis and Charaterization of in situ Crosslinkable Hyaluronic Acid-Based Hydrogels With Potential Applications for Vocal Fold Regeneration," Macromolecules, No. 37, 2004, pp. 3239-3248) to determine the viscoelastic properties of photo-cross-linked hydrogels. An acoustic shaker was used to subject the base of the rod to an oscillatory vertical motion. The motion of the free, top end of the rod was monitored using a laser-Doppler vibrometer. From the measured amplification factor (the amplitude of the velocity at the top of the rod divided by the amplitude of the velocity at the shaker surface), and the phase shift between the top and bottom ends of the rod, the wave propagation solution was used to determine the frequency dependent viscoelastic moduli for the hydrogel. While this method could extend the measurement of viscoelastic properties into the range of phonation frequencies, it could not be used for LP because the LP geometry does not allow the preparation of slender cylindrical specimens.

Accordingly, those skilled in the art desire methods and apparatus for accurately assessing the suitability of candidate materials for use in human vocal fold reconstruction. Since the accurate assessment of the suitability of candidate materials for use in vocal fold reconstruction requires knowledge of the viscoelastic properties of human vocal fold tissue at human phonation frequencies, those skilled in the art also desire methods and apparatus for accurately assessing the viscoelastic properties of human vocal fold materials at phonation frequencies.

In addition, those skilled in the art desire methods and apparatus for accurately assessing the viscoelastic properties of human vocal fold tissues that can be used with practical tissue samples. In order to be feasible, the methods and apparatus must be suitable for use with available tissue sample geometries and dimensions.

Further, efforts are being made to culture human vocal fold material and possibly other living tissues for use in human vocal fold reconstruction. In order to accurately assess the suitability of cultured materials for use in vocal fold reconstruction, an understanding of the effect of the natural environment on tissue growth must be developed. Accordingly, those skilled in the art also desire methods and apparatus for growing human vocal fold tissues in artificial environments similar to natural environments.

SUMMARY OF THE PREFERRED EMBODIMENTS

The foregoing and other problems are overcome, and other advantages are realized, in accordance with the following embodiments of the present invention.

A first alternate embodiment of the present invention comprises a method for measuring the mechanical properties of a sample of soft material, where the sample has a thin, disc-like geometry, the method comprising: mounting the sample of the soft material between two vertically-aligned plates, where a bottom surface of the first of the vertically-aligned plates is attached to a drive shaft of apparatus for twisting the vertically aligned plates and sample, and where a top surface is attached to a bottom surface of the sample, and where a bottom surface of a second of the vertically aligned plates is attached to a top surface of the sample, and where the vertically-aligned plates share a common axis of rotation; at each sample frequency point of a frequency range, twisting the first plate back and forth through an angle and thereby applying a one-dimensional torsional excitation to the sample; after steady state is reached, measuring the rotations of the two plates, and a phase difference between the two plates; calculating an amplification factor from a ratio of the amplitudes of the rotations of the two vertically-aligned plates; and calculating a shear modulus of the sample from the amplification factor and phase difference.

A second alternate embodiment of the present invention comprises an apparatus for measuring the mechanical properties of a sample of soft material, where the sample has a thin, disc-like geometry, the apparatus comprising: a drive motor for applying a twisting motion, the drive motor having a drive shaft, where rotation and frequency of the drive shaft is selectable across a range of discrete frequencies; a pair of vertically-aligned plates comprising a bottom plate and a top plate, the pair of vertically-aligned plates sharing a common axis of rotation, where the bottom plate is mounted on the drive shaft of the drive motor so that an axis of the drive shaft is coincident with the axis of rotation of the pair of vertically-aligned plates, where the pair of vertically-aligned plates are displaced from one another leaving a gap for accepting the sample of the soft material; at least one measuring device for measuring the rotation of the vertically-aligned plates; a computer control coupled to the drive motor and optical measuring device, the computer control comprising at least one memory for storing at least one program for performing operations to measure the mechanical properties of the sample of soft material and at least one processor for executing the program, wherein when the program is executed the following operations are performed: selecting a frequency and maximum angle of rotation to drive the drive motor; driving the drive motor through the selected rotation at the selected frequency; after steady state is reached, measuring the rotation of the two plates; and calculating an amplification factor from a ratio of the amplitudes of the rotations of the two vertically aligned plates.

A third alternate embodiment of the present invention comprises an apparatus for measuring the mechanical properties of a sample of soft material, either natural tissue or a candidate replacement material, in an environment of temperature and relative humidity similar to that experienced by vocal fold tissue in a living human or animal, where the sample has a thin, disc-like geometry, the apparatus comprising: a computer control coupled to the environmental chamber, a drive motor for applying a twisting motion, the drive motor having a drive shaft, where rotation and frequency of the drive shaft is selectable across a range of discrete frequencies; a pair of vertically-aligned, faceted plates comprising a bottom plate and a top plate, the pair of vertically-aligned, faceted plates sharing a common axis of rotation, where the bottom plate is mounted on the drive shaft of the drive motor so that an axis of the drive shaft is coincident with the axis of rotation of the pair of vertically-aligned plates, where the pair of vertically-aligned plates are displaced from one another leaving a gap for accepting a sample of the soft material (either natural tissue or a synthetic material); an optical measuring device for measuring the rotation of at least the top plate; a computer control coupled to the drive motor and optical measuring device, the computer control comprising at least one memory for storing at least one program for performing operations to measure the mechanical properties of the sample of soft material and at least one processor for executing the program, wherein when the program is executed the following operations are performed: selecting conditions for the environmental chamber; selecting a frequency and maximum angle of rotation to drive the drive motor; driving the drive motor through the selected rotation at the selected frequency; after steady state is reached, measuring the rotation of the two plates; and calculating the amplification factor from a ratio of the amplitudes of the rotations of the two vertically aligned plates.

A fourth alternate embodiment of the present invention comprises an apparatus for growing live tissue in an environment similar to that experienced by vocal fold tissue in a living human or animal, the apparatus comprising: an environmental chamber capable of regulating temperature, pressure and humidity in such a way as to reproduce conditions typical in a region of the throat adjacent to the vocal chords; and, positioned in the environmental chamber, growth apparatus for providing a growth environment for vocal fold tissue similar from a vibrational perspective to that experienced by vocal fold tissue in a living human or animal, the apparatus comprising: a drive motor for applying a twisting motion, the drive motor having a drive shaft, where the maximum angle of rotation and the frequency of the drive shaft of the drive motor is selectable across a range of discrete frequencies; a pair of vertically-aligned, faceted plates comprising a bottom plate and a top plate, the pair of vertically-aligned, faceted plates sharing a common axis of rotation, where the bottom plate is mounted on the drive shaft of the drive motor so that an axis of the drive shaft is coincident with the axis of rotation of the pair of vertically-aligned plates, where the pair of vertically-aligned plates are displaced from one another leaving a gap for accepting a disc-like tissue culture media; an optical measuring device for measuring the rotation of at least the top plate; the tissue culture media; a computer control coupled to the environmental chamber, drive motor and optical measuring device, the computer control comprising at least one memory for storing at least one program for performing operations to replicate natural environmental conditions for vocal fold tissue deposited in the tissue culture media, wherein when the program is executed the following operations are performed: selecting conditions for the environmental chamber; selecting a frequency and maximum angle of rotation to drive the drive motor; and driving the drive motor through the selected rotation at the selected frequency.

Thus it is seen that embodiments of the present invention overcome the limitations of the prior art. Certain known methods for measuring the viscoelastic properties of human vocal fold tissue do not extend to human phonation frequencies, and thus cannot be used to generate data for use in assessing the suitability of candidate replacement materials for use in human vocal fold reconstruction. Another known method may be capable of measuring viscoelastic properties at human phonation frequencies, but requires tissue sample geometries not achievable with human vocal fold tissues.

In constrast, the methods and apparatus of the present invention are suitable for use in measuring the viscoelastic properties of vocal fold tissue at human phonation frequencies. Accordingly, the methods and apparatus of the present invention can be used to generate comparison data for use in assessing the suitability of candidate replacement materials for use in human vocal fold reconstruction.

A particular advantage of the methods and apparatus of the present invention is that the methods and apparatus are suitable for use with practical tissue sample geometries. Methods and apparatus that operate at human phonation frequencies are nonetheless impractical if they require sample geometries not achievable with human vocal fold tissue.

BRIEF DESCRIPTION OF THE DRAWINGS

The foregoing and other aspects of these teachings are made more evident in the following Detailed Description of the Preferred Embodiments, when read in conjunction with the attached Drawing FIGS., wherein.

DETAILED DESCRIPTION OF THE PREFERRED EMBODIMENTS

An aspect of the present invention is the use of torsional waves to measure the viscoelastic properties of a cylindrical sample having a thin, disc-like geometry. An advantage of the present invention is that it then becomes possible to measure viscoelastic properties of LP and of candidate replacement materials at human phonation frequencies. Furthermore, because small amplitude torsional waves are described exactly by a one dimensional wave theory the interpretation of the experiments is free of such complications as geometric dispersion and lateral inertia effects that encumber the interpretation of experiments involving longitudinal wave propagation in rods.

In the experiments described herein, results are reported for canine LP, ferret LP, and a number of hyaluronic acid (HA)-based hydrogels. These hydrogel networks exhibit prolonged in vivo residence time, while providing a range of viscoelastic properties that span the range of responses observed for LP tissue. These hydrogels are expected to be biocompatible and to be favorable for promoting cell growth.

Consider the propagation of torsional waves in a cylindrical, viscoelastic sample with its axis lying along the z-direction. The torsional moment or torque at position z at time t can be represented as $$T(z, t) = 2\pi \int_0^a r^2 \tau(z, r, t) dr \tag{3}$$

where a is the radius of the sample and $\tau(z,r,t)$ is the shear stress corresponding to the strain rate history $\partial\gamma(z,r,t)/\partial t$ according to (see J. D. Ferry, *Viscoelastic Properties of Polymers*, $3^{rd}$ Ed., 1980, Wiley and Jones, New York):

$$\tau(z, r, t) = \int_0^t G(t-t') \frac{\partial \gamma(z, r, t')}{\partial t'} dt' \tag{4}$$

where G(t) is the viscoelastic relaxation modulus in shear. Assume that the deformation within the sample can be described adequately as pure torsion in which planes of constant z rotate about the axis of symmetry by an amount $\theta(z,t)$ so that the condition of kinematical compatibility becomes $$\frac{\partial \gamma(z, r, t')}{\partial t'} = \frac{\partial v(z, r, t')}{\partial z} = \frac{\partial \Omega(z, t')}{\partial z} r \tag{5}$$

where v(z,r,t') is the (circumferential) particle velocity and $$\Omega(z, t) = \frac{\partial \theta(z, t)}{\partial t} \tag{6}$$

is the angular velocity of the cross-section.

Substitution of (5) and (4) into (3) gives $$T(z, t) = J \int_0^t G(t - t') \frac{\partial \Omega(z, t')}{\partial z} dt' \tag{7}$$

where $$J = \frac{\pi a^4}{2} \tag{8}$$

is the polar moment of inertia of the cross-sectional area. Consideration of the rate of change of angular momentum for a circular slice of the sample gives the dynamical equation $$\rho J \frac{\partial \Omega(z, t')}{\partial t} = \frac{\partial T(z, t)}{\partial z} \tag{9}$$

where $\rho$ is the mass density of the sample material. Substitution of (6) into (9) gives the following integral-partial-differential equation for the angular velocity $\Omega(z,t)$.

$$\rho \frac{\partial \Omega(z, t')}{\partial t} = \int_0^t G(t - t') \frac{\partial^2 \Omega(z, t')}{\partial z^2} dt' \tag{10}$$

A solution of (10) that vanishes for t<0 and matches measured angular rotations at the two ends of the sample, say z=0 and z=h is sought. More specifically, the objective here is to find the relaxation function G(t) that corresponds to measured angular rotations $\Theta_0(t)$ at z=0 and $\Theta_h(t)$ at z=h. Just as the direct problem requires an additional boundary condition at z=h to predict the motion $\Omega_h(t)$ from the motion $\Omega_0(t)$ and the function G(t), the determination of G(t) from $\Omega_0(t)$ and $\Omega_h(t)$ requires an additional boundary condition at z=h. This additional boundary condition expresses the nature of the restraint at z=h.

For interpretation of experimental results on a cylindrical sample sandwiched between two rigid plates the cylindrical sample to be attached to a rigid plate at z=h is considered. The rigid plate is taken to have density $\rho_0$ and polar moment of inertia $I_0$. The plate is assumed to be bonded to the cylindrical viscoelastic sample at z=h, but is otherwise free. The dynamical equation for the angular acceleration of the rigid plate gives the following boundary condition at z=h.

$$-J \int_0^t G(t-t') \frac{\partial \Omega(z, t')}{\partial z} \bigg|_{z=h} dt' = \rho_0 I_0 \frac{\partial \Omega(h, t)}{\partial t} \tag{11}$$

To solve Eqns. (10) and (11) the Laplace transform is taken of the field equation (10) and the boundary condition (11) to obtain $$\rho s \tilde{\Omega}(z, s) = \tilde{G}(s) \frac{\partial^2 \tilde{\Omega}(z, s)}{\partial z^2} \tag{12}$$

and $$-J\tilde{G}(s) \frac{\partial \tilde{\Omega}(h, s)}{\partial z} = \rho_0 I_0 s^2 \tilde{\theta}(h, s) \tag{13}$$

respectively, where a superposed ~ denotes the Laplace transform of the underlying function. Replacement of $\tilde{\Omega}$ by $s\tilde{\theta}$ in (12) and (13) gives the ordinary differential equation for $\tilde{\theta}(z,s)$, $$\rho s \tilde{\theta}(z, s) = \tilde{G}(s) \frac{\partial^2 \tilde{\theta}(z, s)}{\partial z^2} \tag{14}$$

and the boundary condition, $$-J\tilde{G}(s) \frac{\partial \tilde{\theta}(h, s)}{\partial z} = \rho_0 I_0 s \tilde{\theta}(h, s) \tag{15}$$

Equation (14) has a solution of the form, $$\tilde{\theta}(z,s) = A \cosh(\lambda z) + B \sinh(\lambda z) \tag{16}$$

where $$\lambda(s) = \sqrt{\rho s / \tilde{G}(s)} \tag{17}$$

and the coefficients A and B are to be determined from the boundary condition (15) and the imposed motion at z=0. It is assumed that the imposed motion is the harmonic motion $$\theta(0,t) = \theta_0 \exp(i\omega_0 t) \tag{18}$$

where $\theta_0$ and $\omega_0$ are constants.

The coefficient A obtained by the substitution of (16) into the Laplace transform of (18) is $$A(s) = \frac{\theta_0}{s - i\omega_0} \tag{19}$$

From the boundary condition (15), and the relation (19), the coefficient B is $$B = -\frac{J\tilde{G}(s)\lambda(s)\sinh[\lambda(s)h] + \rho_0 I_0 s \cosh[\lambda(s)h]}{J\tilde{G}(s)\lambda(s)\cosh[\lambda(s)h] + \rho_0 I_0 s \sinh[\lambda(s)h]} \frac{\theta_0}{(s - i\omega_0)} \tag{20}$$

To invert the Laplace transform $\tilde{\theta}(h,s)$ the definition of the inverse transform is used:

$$\theta(h, t) = \frac{1}{2\pi i} \int_{\varepsilon-j\infty}^{\varepsilon+j\infty} \exp(st)\tilde{\theta}(h, s) \quad (21)$$

The parameter $\epsilon$ is a positive real number so the integration path is to the right of the imaginary axis in the s-plane. The integration contour can be closed in the left half plane. No contribution is obtained from either the contour at $\infty$ or from the integrals along branch cuts, in view of the form of the expressions (16), (17), (19), (20). Therefore, by the Residue Theorem, the integral (21) is simply equal to $2\pi i$ times the sum of the residues of the integrand at poles to the left of $s=\epsilon$. The only pole is at $s=i\omega_0$. Here $$\lambda(i\omega_0) = \sqrt{\frac{\rho i \omega_0}{\tilde{G}(i\omega_0)}} = i\sqrt{\frac{\rho \omega_0^2}{G*(\omega_0)}} \quad (22)$$

in which (e.g. Ferry, 1980)

$$G*(\omega_0) \equiv i\omega_0 \tilde{G}(i\omega_0) \quad (23)$$

is the complex modulus for the viscoelastic response of the sample material in simple shear at circular frequency $\omega_0$. Characterization of the viscoelastic response can be put into more readily interpretable form by representing the complex modulus in terms of its magnitude $|G*(\omega)|$ and its phase angle $\delta(\omega)$:

$$G*(\omega)=|G*(\omega)|e^{i\delta(\omega)} \quad (24)$$

In writing the solution it is helpful to simplify the argument to $$\lambda h = i(\xi\alpha - i\xi\beta) \quad (25)$$

where $$\xi = \omega_0 h \sqrt{\frac{\rho}{|G*(\omega_0)|}}, \alpha = \cos\left(\frac{\delta(\omega_0)}{2}\right), \beta = \sin\left(\frac{\delta(\omega_0)}{2}\right).$$

Then, the angular velocity at the end $z=h$ can be written in the form $$\theta(h,t)=M(\omega_0)\theta_0 \cos(\omega_0 t - \phi(\omega_0)) \quad (26)$$

in which $M(\omega_0)$ is the amplification factor:

$$M = \frac{c\sqrt{(c\cos(\xi\alpha) - d\sin(\xi\alpha))^2 + (c^2 + d^2)\sinh^2(\xi\beta)}}{\sqrt{(c\cos(\xi\alpha) + d\sin(\xi\alpha))^2 + (c^2 + d^2)\sinh^2(\xi\beta)}}$$

where $$c = c(\omega_0) \equiv J\sqrt{|G*(\omega_0)|\rho}$$

$$d = d(\omega_0) \equiv \rho_0 I_0 \omega_0$$

and $\phi(\omega_0)$ is the phase shift characterized by $$\tan(\phi(\omega_0)) = \frac{(c\sin(\xi\alpha) + d\cos(\xi\alpha))\sinh(\xi\beta)}{(c\cos(\xi\alpha) - d\sin(\xi\alpha))\cosh(\xi\beta)}$$

Alternatively, the analysis could be carried out in the frequency domain by considering a harmonic excitation of the form (18). In either case the result of the torsional wave analysis is the response functions $M(\omega_0)$ and $\phi(\omega_0)$. If the response $M(\omega_0)$, $\phi(\omega_0)$ is measured over a range of frequencies $\omega_0$, then the frequency dependence of the moduli $|G*(\omega_0)|$, $\delta(\omega_0)$ can be estimated by means of a regression analysis. Parameter values in the regression models are readily obtained using an Excel spreadsheet and minimizing the differences between calculated and measured values by using the Solver routine.

Figures 1A, 1B:
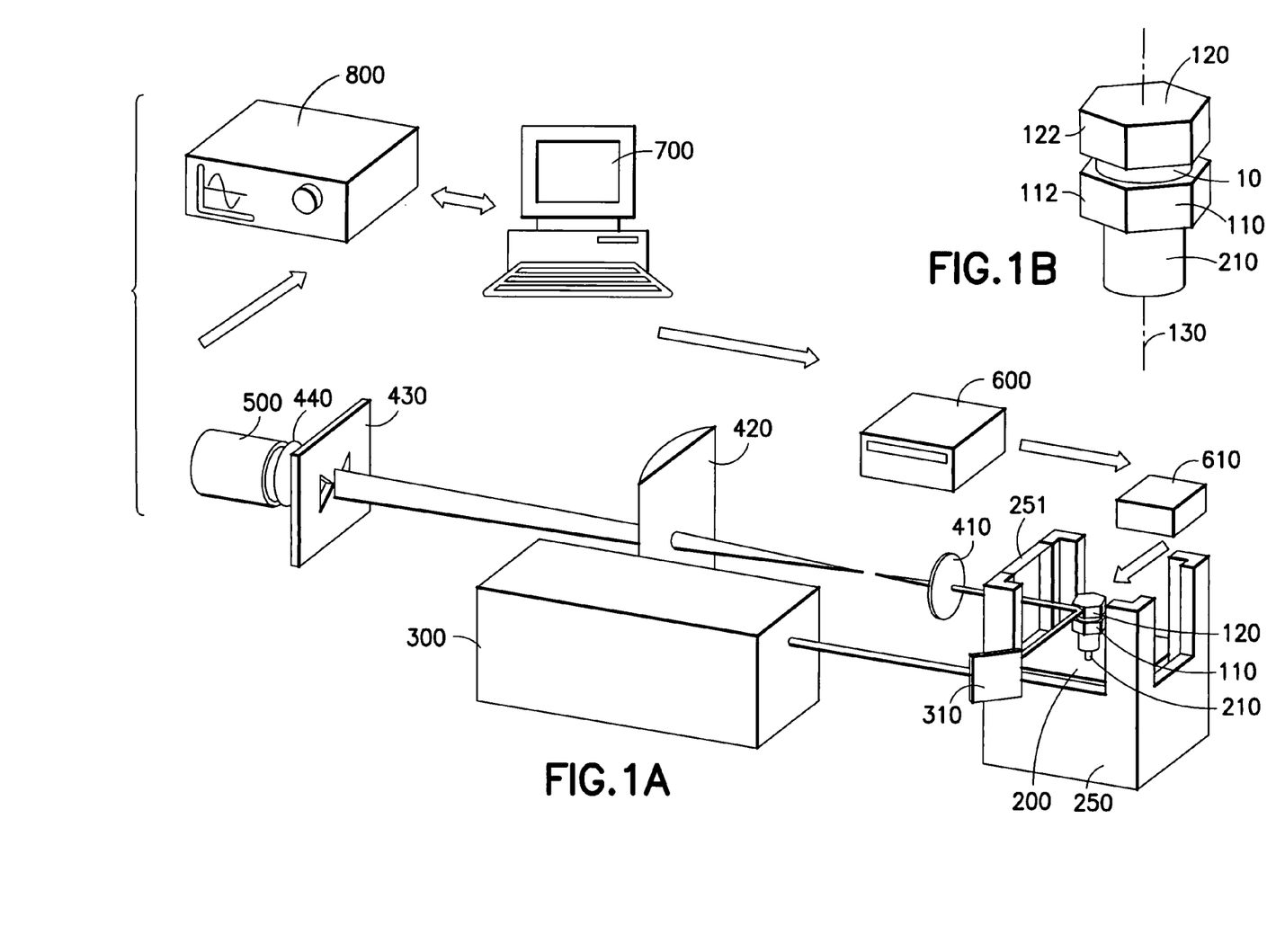
FIGS. 1A and 1B depict—in perspective, conceptual views—apparatus in accordance with the present invention for measuring the mechanical properties of soft materials.
Figure 2:
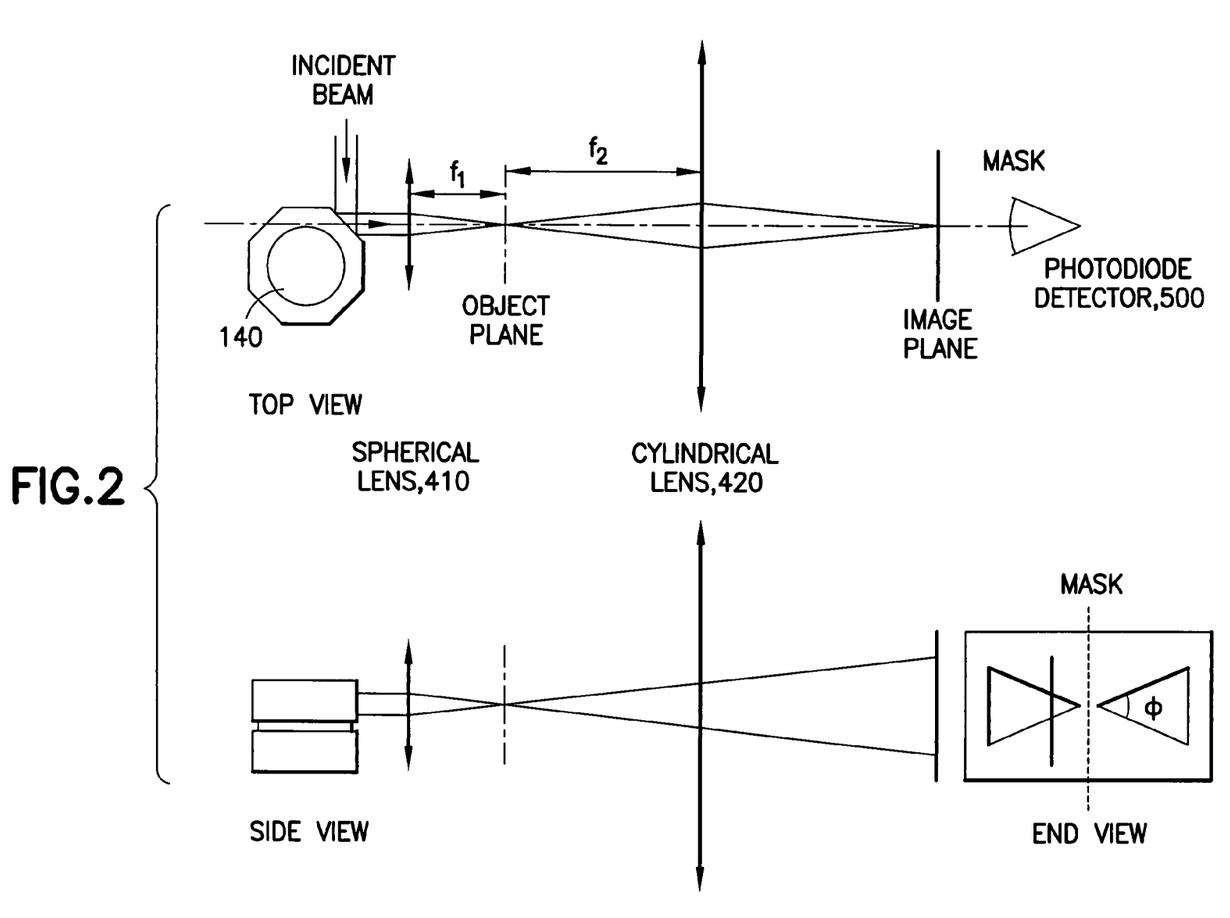
FIG. 2 depicts top, side and end view of an optical layout in accordance with the present invention for measuring the mechanical properties of soft materials.

An apparatus for measuring the mechanical properties of soft materials in accordance with the present invention is shown in FIGS. 1-2. A thin cylindrical sample 10 of a soft material is placed between two faceted plates 110, 120 as shown in FIG. 1B; in the example depicted in FIGS. 1-2 the plates are hexagonal. The hexagonal plates 110, 120 are vertically aligned and share a common axis of rotation 130. The bottom plate 110 is mounted on a drive shaft 210 of a drive motor 200. In the example depicted in FIGS. 1-2 the drive motor 200 comprises a galvanometer obtained from a commercially available optical scanner, although other precision drive motors can be used in accordance with the present invention. The axis of the drive shaft 210 of the optical scanner 200 is coincident with the common axis of rotation 130 of the pair of vertically-aligned, faceted plates 110, 120. The bottom plate is rotated back and forth through angles up to ±6° by means of the galvanometer (for example, GSI Lumonics, optical scanner Model 000-G112) at frequencies up to 2500 Hz. To ensure that the shear strains in the sample are sufficiently small for linear viscoelasticity to be a satisfactory approximation, the imposed rotations are kept less than ±0.2°.

The rotations of the top 120 and bottom 110 plates are monitored by an optical lever technique in which laser beams, generated by laser 300, are first reflected by a mirror 310; and then by the aluminized, faceted faces 112, 122 of the hexagonal plates. The reflected laser light then passes through a spherical lens 410, a cylindrical lens 420, a butterfly-shaped aperture 430 and a collecting lens 440 before being captured by photodiode detectors 500. The spherical lens 410 expands the beam and the cylindrical lens 420 focuses the beam into a vertical sheet of light at the aperture 430. The spherical lens 410 is selected to ensure that the height of the sheet of light at the aperture is greater than the maximum height of the aperture. Because of the shape of the aperture (See End View in FIG. 2) the light power collected, and consequently the output of each photodiode 500, is proportional to the angular rotation of the respective plate.

Although an optical lever technique is used to measure the rotations of the top 120 and bottom 110 plates in the embodiment depicted in FIGS. 1A and 1B, other methods could be used. For example, the rotation of the bottom plate 110 could be controlled by controlling the rotation of the drive shaft 210.

The rotation of the bottom plate 110 is driven by the drive shaft 210 of the drive motor, which in turn is driven by a frequency generator 600 and amplifier 610 controlled by a computer 700. The frequency generator 600 steps through a sequence of frequencies from a minimum frequency, $f_{min}$, to a maximum frequency, $f_{max}$, in steps $\Delta f$. At each frequency the amplitude of the rotation of each plate 110, 120 is obtained as the average amplitude over a fixed number of cycles, usually 10, after transients from the change in frequency have died out. The output of the photodiodes 500 is monitored by an oscilloscope 800 (Agilent 54622A) that provides directly the average amplitude of the signal, less its minimum value. The difference between these two quantities is proportional to the rotation of the respective plate.

The experimentally determined amplification factor is obtained as the ratio of the amplitude of the rotation of the top plate 120 divided by that of the bottom plate 110. Calibration differences between the recorded outputs for the two plates 110, 120 are accounted for by adjusting the experimentally determined amplification factor to approach the required value of unity as the frequency goes to zero.

Amplification factors for each frequency, determined from the experimental records as described above, are compared with those predicted by the viscoelasticity model described in the previous section. For that model the viscoelastic description of the material is expressed in terms of the amplitude of the complex shear modulus, $|G^*(\omega)|$, and the loss angle, $\delta(\omega)$. The height and diameter of the sample, required for the wave analysis, are obtained from digital images of the sample in place. The output signal shows a peak in the amplification factor at a frequency, $f_{peak}$. For each test, a constant modulus $|G^*|$ and phase shift $\delta$ are obtained that provide the best fit between the model and the experimental results over a range of frequencies spanning the frequency, $f_{peak}$.

In the embodiment depicted in FIGS. 1A-1B, the sample 10 and vertically-aligned plates 110, 120 are placed within an environmental chamber 250. The environmental chamber 250 depicted in FIG. 1A is shown in a partial cut-away view; in actual operation the environmental chamber 250 would be sealed and would provide controllable conditions of temperature and relative humidity. The environmental chamber 250 has transparent sides 251 formed of glass or other suitable transparent material, which permits the laser light generated by laser 300 to pass through. In embodiments of the present invention the conditions of temperature and humidity would be controlled by computer 700 which would be programmed to duplicate conditions encountered in the throat of a living human or animal. In other embodiments, the environmental chamber may be deleted.

In still further embodiments, the present invention could be used to culture living vocal fold material. In such embodiments a suitable tissue culture media would be placed between the vertically aligned plates 110, 120 and vocal fold cells would be introduced into the tissue culture media. The controllable conditions of temperature and humidity created by the environmental chamber 250, as well as vibrational conditions created by the torsional excitation method of the present invention, would provide a growth environment very similar to that encountered in the throats of living humans or animals.

Figure 3:
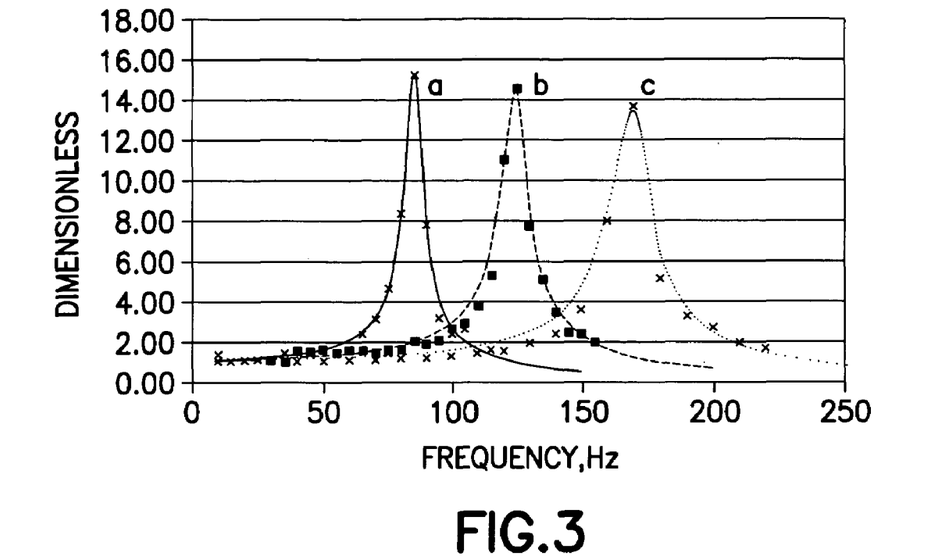
FIG. 3 is a graph depicting experimental results showing the frequency dependence of amplification factors for three synthetic hydrogels.

An example of results for HA-based hydrogels is shown in FIG. 3. Hydrogel compositions and geometries, and the viscoelastic moduli that provided the best fist between model predictions and experimental results are:
(a) HAGMA (2%), h=0.969 mm, a=2.52 mm, $G_1$=1514 Pa, $\delta$=0.127 radians.
(b) HAGMA (2%)/PEGDA[MW=575](6%), h=0.997 mm, a=2.54 mm, $G_1$=3230 Pa, $\delta$=0.132 radians.
(c) HAGMA (2%) PEGDA[MW=2000](12%), h=0.969 mm, a=2.51 mm, $G_1$=6066 Pa, $\delta$=0.14 radians.

HAGMA is glycidyl methacrylate modified hyaluronic acid, and PEGDA is polyethylene glycol diacrylate. Inset shows the sample (c) between the two plates of the loading system. The cylindrical samples were punched out of sheets, synthesized in a flat-bottomed container and cross-linked using a UV light source. Tests were conducted under conditions of ambient temperature and humidity. Close agreement between the results of the experiment and the predictions of the model for constant values of the viscoelastic parameters $(G_1, \delta)$ suggests the validity of the model and the relatively weak dependence of these parameters on frequency over a range of frequencies comparable to the widths of the peaks, say 50 Hz. The increase in modulus with increasing fractions of PEGDA is consistent with expectations of the stiffening effect of this additive. Results are repeatable for successive tests on the same sample as long as the time between tests is not so long that the moisture content of the sample changes significantly. Results are also reproducible for separate samples prepared in the same way.

Figure 4:
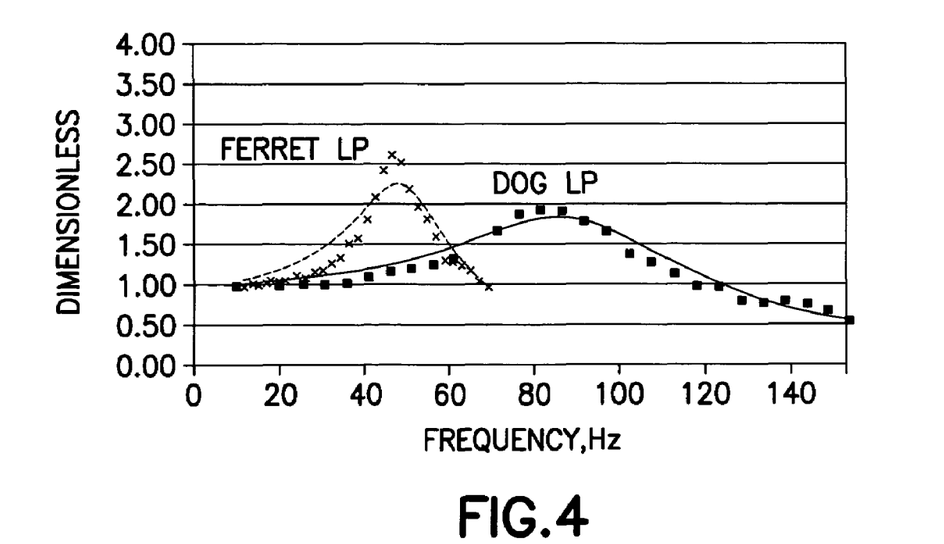
FIG. 4 is a graph depicting experimental results showing the frequency dependence of amplification factors for vocal fold materials obtained from a dog and a ferret.

Examples of results for lamina propria samples taken from a dog larynx and from a ferret larynx are shown in FIG. 4. Samples were prepared by separating the LP from the vocalis muscle and then punching out a cylindrical sample with a thickness equal to the full thickness of the LP. Again the tests were conducted under conditions of ambient temperature and humidity. The sample geometries and results are as follows:
Dog LP: h=0.371 mm, a=1.74 mm, $G_1$=1423 Pa, $\delta$=0.898 radians
Ferret LP: h=0.27 mm, a=1.43 mm, $G_1$=1944 Pa, $\delta$=1.131 radians The fit between model and experiment is not as good as that shown in FIG. 3 for hydrogels. Better agreement can be obtained by including weak dependence of the viscoelastic moduli on frequency. Nevertheless, the agreement is sufficiently good to give confidence in the approximate levels of the complex modulus characterized by the parameters ($G_1$, $\delta$). Much lower peak values for the amplification factors result in much larger values for the loss angles $\delta$.

Thus it is seen that the foregoing description has provided by way of exemplary and non-limiting examples a full and informative description of the best method and apparatus presently contemplated by the inventors for measuring the mechanical properties of soft materials. One skilled in the art will appreciate that the various embodiments described herein can be practiced individually; in combination with one or more other embodiments described herein; or in combination with interactive tabular query interfaces differing from those described herein. Further, one skilled in the art will appreciate that the present invention can be practiced by other than the described embodiments; that these described embodiments are presented for the purposes of illustration and not of limitation; and that the present invention is therefore limited only by the claims which follow.

We claim:

1. A method for measuring the mechanical properties of a sample of soft material, where the sample has a thin, disc-like geometry, the method comprising:
mounting the sample of the soft material between two vertically-aligned plates, where a bottom surface of the first of the vertically-aligned plates is attached to a drive shaft of apparatus for twisting the vertically aligned plates and sample, and where a top surface is attached to a bottom surface of the sample, and where a bottom surface of a second of the vertically aligned plates is attached to a top surface of the sample, and where the vertically-aligned plates share a common axis of rotation;

at each sample frequency point of a frequency range, twisting the first plate back and forth through an angle and thereby applying a one-dimensional torsional excitation to the sample;

after steady state is reached, measuring the rotations of the two plates, and a phase difference between the two plates;

calculating an amplification factor from a ratio of the amplitudes of the rotations of the two vertically-aligned plates; and calculating a shear modulus of the sample from the amplification factor and phase difference.

2. The method of claim 1 where the soft material is a natural tissue.

3. The method of claim 2 where the natural tissue is vocal fold material.

4. The method of claim 3 where the vocal fold material is human vocal fold material.

5. The method of claim 3 where the vocal fold material is animal vocal fold material.

6. The method of claim 1 where the soft material is a synthetic material.

7. The method of claim 6 where the synthetic material is a candidate material for use in human vocal fold reconstruction.

8. The method of claim 1 where the frequency range corresponds to at least a portion of a human phonation frequency range.

9. The method of claim 8 where the frequency range is 100-900 Hz.

10. The method of claim 1, where the rotation of the two plates is measured using an optical lever method.

11. The method of claim 1, where the rotation of the first vertically-aligned plate is measured by controlling the rotation of the drive shaft.

12. Apparatus for measuring the mechanical properties of a sample of soft material, where the sample has a thin, disc-like geometry, the apparatus comprising:
   a drive motor for applying a twisting motion, the drive motor having a drive shaft, where the maximum angle of rotation and frequency of the drive shaft is selectable across a range of angles and frequencies;
   a pair of vertically-aligned plates comprising a bottom plate and a top plate, the pair of vertically-aligned plates sharing a common axis of rotation, where the bottom plate is mounted on the drive shaft of the drive motor so that an axis of the drive shaft is coincident with the axis of rotation of the pair of vertically-aligned plates, and where the pair of vertically-aligned plates are displaced from one another leaving a gap for accepting the sample of the soft material;
   at least one measuring device for measuring the rotation of the vertically-aligned plates;
   a computer control coupled to the drive motor and optical measuring device, the computer control comprising at least one memory for storing at least one program for performing operations to measure the mechanical properties of the sample of soft material and at least one processor for executing the program, wherein when the program is executed the following operations are performed:
      selecting a frequency and maximum angle of rotation to drive the drive motor;
      driving the drive motor through the selected rotation at the selected frequency;
      after steady state is reached, measuring amplitudes of rotation of each of the two plates; and
      calculating an amplification factor from a ratio of the amplitudes of rotation of the two vertically aligned plates.

13. The apparatus of claim 12 where the following additional operations are performed:
   after steady state is reached, measuring a phase difference between the two plates;
   selecting a plurality of additional frequencies;
      for each of the selected additional frequencies, driving the drive motor at the selected frequency;
      measuring amplitudes of rotation of each of the two plates and the phase difference between the two plates at the selected frequency;
      calculating the amplification factor at the selected frequency; and
   calculating a shear modulus of the sample from the amplification factors and phase differences observed at the selected frequencies.

14. The apparatus of claim 12 where the pair of vertically-aligned plates are faceted, and where at least one measuring device for measuring the rotation of the pair of vertically-aligned plates operates according to an optical lever method.

15. The apparatus of claim 14 where at least one measuring device further comprises:
   a laser for generating laser light to be reflected off the facets of the pair of vertically-aligned plates;
   a detector for detecting laser light reflected off the facets of the pair of vertically-aligned plates; and
   optics for focusing the reflected laser light on the detector.

16. The apparatus of claim 12 where the at least one measuring device for measuring the rotation of the pair of vertically-aligned plates measures the rotation of the bottom plate by measuring the rotation of the drive shaft of the drive motor.

17. The apparatus of claim 12 where the soft material is a natural tissue.

18. The apparatus of claim 17 where the natural tissue is vocal fold tissue.

19. The apparatus of claim 18 where the vocal fold tissue is human vocal fold tissue.

20. The apparatus of claim 18 where the vocal fold tissue is animal vocal fold tissue.

21. The apparatus of claim 12 where the soft material is a synthetic material.

22. The apparatus of claim 21 where the synthetic material is a candidate material for use in vocal fold reconstruction.

23. The apparatus of claim 12 where the frequency range corresponds to at least a portion of a human phonation frequency range.

24. The apparatus of claim 23, where the frequency range is 100-900 Hz.

25. The apparatus of claim 12 where the apparatus includes an environmental chamber for maintaining the sample at a temperature and relative humidity of vocal folds in a living subject.

26. The apparatus of claim 25 where the living subject is human, whereby the environmental chamber replicates conditions of temperature and relative humidity experienced by vocal folds in a human subject.

27. The apparatus of claim 25 where the living subject is animal, whereby the environmental chamber replicates conditions of temperature and relative humidity experienced by vocal folds in an animal subject.

28. Apparatus for growing live tissue in an environment similar to that experienced by vocal fold tissue in a living subject, the apparatus comprising:
an environmental chamber capable of regulating temperature, pressure and humidity in such a way as to reproduce conditions typical in a region of the throat adjacent to the vocal chords; and, positioned in the environmental chamber,
growth apparatus for providing a growth environment for vocal fold tissue similar from a vibrational perspective to that experienced by vocal fold tissue in a living subject, the apparatus comprising:
a drive motor for applying a twisting motion, the drive motor having a drive shaft, where the maximum angle of rotation and the frequency of the drive shaft of the drive motor is selectable across a range of discrete frequencies;
a pair of vertically-aligned, faceted plates comprising a bottom plate and a top plate, the pair of vertically-aligned, faceted plates sharing a common axis of rotation, where the bottom plate is mounted on the drive shaft of the drive motor so that an axis of the drive shaft is coincident with the axis of rotation of the pair of vertically-aligned plates, where the pair of vertically-aligned plates are displaced from one another leaving a gap for accepting a disc-like tissue culture media;
an optical measuring device for measuring the rotation of at least the top plate;
the tissue culture media;
a computer control coupled to the environmental chamber, drive motor and optical measuring device, the computer control comprising at least one memory for storing at least one program for performing operations to replicate natural environmental conditions for vocal fold tissue deposited in the tissue culture media, wherein when the program is executed the following operations are performed:
selecting conditions for the environmental chamber;
selecting a frequency and maximum rotation to drive the drive motor; and
driving the drive motor through the selected rotation at the selected frequency.

29. The apparatus of claim 28 where the selected frequency is within the human phonation frequency range.

30. The apparatus of claim 28 where the living subject is human, whereby the environmental chamber replicates conditions of temperature and relative humidity experienced by vocal folds in a human subject.

31. The apparatus of claim 28 where the living subject is animal, whereby the environmental chamber replicates conditions of temperature and relative humidity experienced by vocal folds in an animal subject.

* * * * *